United States Patent
Tethrake et al.

(10) Patent No.: US 7,256,699 B2
(45) Date of Patent: Aug. 14, 2007

(54) BUTTON-TYPE RFID TAG

(75) Inventors: Steven M. Tethrake, North Webster, IN (US); Robert Varner, Germantown, TN (US); Jeffrey H. Nycz, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 161 days.

(21) Appl. No.: 11/089,003

(22) Filed: Mar. 24, 2005

(65) Prior Publication Data

US 2006/0214791 A1  Sep. 28, 2006

(51) Int. Cl.
*G08B 13/14* (2006.01)

(52) U.S. Cl. .................. 340/572.8; 340/572.1; 340/10.1

(58) Field of Classification Search ........... 340/572.1
See application file for complete search history.

(56) References Cited

U.S. PATENT DOCUMENTS

| | | | |
|---|---|---|---|
| 4,075,632 A | 2/1978 | Baldwin et al. | |
| 4,360,801 A | 11/1982 | Duhame | |
| 4,390,880 A | 6/1983 | Henoch | |
| 4,739,328 A | 4/1988 | Koelle et al. | |
| 5,030,807 A | 7/1991 | Landt et al. | |
| 5,057,095 A * | 10/1991 | Fabian | 340/572.5 |
| 5,781,112 A * | 7/1998 | Shymko et al. | 340/572.8 |
| 5,825,298 A * | 10/1998 | Walter | 340/825.49 |
| 5,825,303 A * | 10/1998 | Bloss et al. | 340/870.02 |
| 5,880,675 A * | 3/1999 | Trautner | 340/572.8 |
| 6,104,295 A | 8/2000 | Gaisser et al. | |
| 6,191,691 B1 * | 2/2001 | Serrault | 340/572.8 |
| 6,239,737 B1 * | 5/2001 | Black | 342/51 |
| 6,255,949 B1 | 7/2001 | Nicholson et al. | |
| 6,366,206 B1 * | 4/2002 | Ishikawa et al. | 340/572.1 |
| 6,452,497 B1 * | 9/2002 | Finlayson | 340/572.8 |
| 6,462,661 B2 * | 10/2002 | Pfeiffer et al. | 340/572.8 |
| 6,843,628 B1 * | 1/2005 | Hoffmeister et al. | 411/14 |
| 6,888,458 B2 * | 5/2005 | Carlson | 340/540 |
| 6,989,749 B2 * | 1/2006 | Mohr | 340/572.1 |
| 2006/0022056 A1 * | 2/2006 | Sakama et al. | 235/492 |
| 2006/0097872 A1 * | 5/2006 | Ho | 340/572.1 |
| 2006/0186210 A1 * | 8/2006 | Tethrake et al. | 235/492 |

FOREIGN PATENT DOCUMENTS

DE  19912806 A1 * 9/2000
EP  0535919 A * 4/1993

* cited by examiner

*Primary Examiner*—Benjamin C. Lee
*Assistant Examiner*—Eric M. Blount
(74) *Attorney, Agent, or Firm*—Hunton & Williams LLP

(57) ABSTRACT

An RFID tag that is integrated into button-type, substantially cylindrically-shaped housing with a portion for attaching the tag to an object to be identified through radio frequency identification techniques.

31 Claims, 4 Drawing Sheets

BUTTON-TYPE RFID TAG

FIELD OF THE INVENTION

Embodiments of the invention generally relate to radio frequency identification systems, and more particularly to a button-type, threaded RFID transponder tag for easy attachment, detachment and reattachment to a variety of different shaped devices and equipment. The button-type, threaded RFID transponder tag may be particularly suited for application to medical and surgical devices and equipment.

Description of Related Art

Electronic data carrying memory devices are known. These devices provide a means for tracking and providing information about tools, equipment, inventory and other items. Memory devices permit linking of large amounts of data with an object or item. They typically include a memory and logic in the form of an integrated circuit ("IC") and a mechanism for transmitting data to and/or from the product or item attached to the memory device. An example of such a memory device-based product identification technology is radio frequency identification (RFID).

Radio frequency identification (RFID) systems use an RF field generator (reader) and a plurality of RFID transponder tags that store information about the goods and products to which they are attached. RFID tags are miniature electronic circuits that typically consist of a coil that acts as an antenna and a small silicon-based microprocessor with a memory, all encapsulated in a sealing material. RFID tags store identification information, usually in the form of an identification number that corresponds to an object or item to which the tag is attached. When a transponder tag enters an RF field generated by a reader device, the circuit of the tag becomes energized causing the processor to perform a data operation, usually by emitting a signal containing the processor's stored information. The basic structure and operation of RFID tags can be found in, for example, U.S. Pat. Nos. 4,075,632, 4,360,801, 4,390,880, 4,739,328 and 5,030,807, the disclosures of which are hereby incorporated by reference in their entirety.

RFID tags generally are formed on a substrate, such as, paper, and can include analog RF circuits, digital logic, and memory circuits. RFID tags also can include a number of discrete components, such as capacitors, transistors, and diodes. RFID tags are categorized as either active or passive. Active tags have their own discrete power source such as a battery. When an active tag enters an RF field it is turned on and then emits a signal containing its stored information. Passive tags do not contain a discrete power source. Rather, they become inductively or capacitively charged when they enter an RF field. Once the RF field has activated the passive circuit, the passive tag emits a signal containing its stored information. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, both passive and active dynamic RFID tags can permit new or additional information to be stored in the RFID tag's memory, or can permit the RFID tag to manipulate data or perform some additional functions.

Though originally invented to track feeding of cattle, RFID tags are today utilized in a variety of applications including retail security, inventory management, and even computerized checkout. With the price of RFID tags now reaching as low as 5 cents per tag, and because of reductions in size due to an overall trend towards miniaturization in circuit design, RFID tags currently are being applied to many types of products, both at the consumer level as well as in manufacturing processes. RFID tags enable manufacturers to wirelessly track products from the manufacturing stage to the point-of-sale. They provide a robust, cost effective, efficient and accurate solution to inventory tracking and management.

Commercially available RFID tags, both active and passive, generally come in one of two configurations: inductively or capacitively coupled. Inductively coupled tags, the first type of RFID tags developed, consist of a silicon-based microprocessor, a metal coil wound into a circular pattern that serves as the tag's antenna, and an encapsulating material that wraps around the chip and coil. These tags are powered by an electromagnetic field generated by the tag reader. The tag's antenna picks up the electromagnetic energy which in turn powers the chip. The tag then modulates the electromagnetic field in order to transmit data back to the reader. Despite advances in silicon manufacturing processes, inductively coupled tags have remained relatively expensive due to the coil antenna and the manufacturing process required to wind the coil around the surface of the tag.

The second type of RFID tags are capacitively coupled RFID tags. Capacitively coupled tags eliminate the metal coil, consisting instead of a silicon microprocessor, paper substrate, and a conductive carbon ink that is applied to the paper substrate through a conventional printing means. By using conductive ink and conventional printing processes, a relatively low cost, disposable tag can be created that is easily integrated into conventional product labels.

RFID tags are rapidly becoming the preferred method of inventory tracking in retail and distribution applications and will likely surpass bar codes as the preferred point-of-sale checkout identifier. Large retail chains such as WALMART Corporation are already requiring their suppliers to utilize RFID tags for tracking shipments. RFID tags have significant advantages over bar code labels. For example, bar codes are limited in size by resolution limitations of bar code scanners, and the amount of information that the symbols can contain is limited by the physical space constraints of the label. Therefore, some objects may be unable to accommodate bar code labels because of their size and physical configuration. In contrast, RFID tags store their information in digital memory. Thus, they can be made much smaller than bar code tags.

Another advantage of RFID tags over bar codes is that bar code readers require line of sight in order to read the reflection pattern from a bar code. As labels become worn or damaged, they can no longer be read with the bar code scanner. Also, because a person operating the bar code scanner must physically orient either the scanner or the product to achieve line of sight on each item being scanned, items must be scanned one at a time resulting in prolonged scan time. RFID tags, on the other hand, are read through radio waves, which do no require line of sight because they are able to penetrate light impermeable materials. This not only eliminates the line of sight requirement, but also allows rapid identification of a batch of tagged products.

Yet another relative advantage of RFID tags over bar code labels is that for dynamic RFID tags, the information stored in the tag may be updated using a writing device to wirelessly transmit the new information to be stored. Updating information in bar code tags typically requires printing a new tag to replace the old.

One problem associated with the use of RFID tags, which also is common to bar code tags, is that it can be difficult to securely attach the tags to various goods and products. As discussed above, capacitively coupled RFID tags usually are printed on a paper substrate and then attached to various items using an adhesive bonding. However, in some applications, a paper tag may not hold up to the rigors of the environment in which the product is used. For example, in the field of medical equipment, and in particular, surgical instruments and surgical instrument storage and sterilization systems, items are routinely exposed to environments containing various combinations of high temperatures, high pressure and liquid, vaporous and/or gaseous chemical sterilants. Over time, a paper RFID tag would not provide reliable performance under these harsh conditions. More rugged RFID tags have been developed as a potential solution to this problem. An example of a rugged RFID tag is provided in U.S. Pat. No. 6,255,949, the disclosure of which is hereby incorporated by reference in its entirety. The '949 patent discloses an RF transponder tag surrounded by a thermally resistant polymer and encapsulated in a hardened case. Because radio frequency waves can penetrate such materials, performance of the tag is not degraded by the case or polymer. Such a configuration is said to prevent damage to the transponder tag if exposed to high temperature environments.

While making the tag enclosure more rugged may sometimes protect the internal components of the tag, this still does not solve the problem of keeping the tag securely attached, particularly in harsh environments. As discussed above, substrate-based tags, even ruggedized tags, are typically mounted using an adhesive. This presents at least two problems for the application of tags exposed to harsh environments. First, adhesives will break down and lose their adhesive property when they are exposed to heat and moisture. This limits their usage to dry "friendly" environments. Second, adhesives typically require a flat surface on which to mount the RFID tags. This precludes the mounting of tags onto devices, equipments, or containers that do not have a flat surface of sufficient dimensions. Furthermore, many items do not have geometrically shaped portions sufficiently large to accommodate such a substrate-based tag. Thus, for at least these reasons, adhesives do not provide an effective solution for attaching RFID tags in certain environments.

A proposed solution to the above described attachment problem has been to integrate the RFID tag into a bracelet or strap. This can be particularly useful for patient or personal monitoring systems. U.S. Pat. No. 6,104,295 describes such an electronic band having an integral RFID tag. However, a problem with this solution is that the band's width will preclude application of the bracelet to small items. Also, because the portion of the band defined by the tag is rigid, this will dictate the minimum width that the band strap can be adjusted to. Thus, for items having a small diameter, only a loose fitting will be possible.

The problems of attachment as well as ruggedization are particularly acute in the field of medical equipment and instruments. Surgical equipment, including surgical instruments, kits and other medical equipment must be regularly exposed to heat as well as liquid and/or vaporous chemicals during the sterilization process. Also, this equipment is typically expensive and highly mobile. One contemplated solution for implementing RFID tagging of surgical equipment and other devices requiring sterilization is to embed RFID tags in a portion of the item during the manufacturing process. However, this solution is very expensive, difficult to implement, and precludes retrofitting of existing equipment. Also, because the tag is permanently embedded, if the tag stops functioning, the item must be discarded or else can no longer be tracked using RFID technology. Another, problem with embedded tags is that the high metal content of the item being tagged causes current losses that impeded reading and writing operations.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

There is a need for accurate and efficient tracking that does not impede or interfere with the sterilization process.

Based on the foregoing, it would be desirable to provide an RFID tag that overcomes or ameliorates some or all of the shortcomings of conventional tags. In particular, it would be desirable to provide an RFID tag that can withstand the rigors of sterilization and other harsh environments and that can be cheaply and easily used, attached, and replaced to surgical instruments and other equipment equipment.

Thus, it is a feature of various embodiments of the invention to provide an RFID tag that is sufficiently ruggedized to permit use of the tag in moist, heated, cooled, pressurized or other destructive environments. It is a further feature of various embodiments of the invention to provide an RFID tag that provides secure attachment, but can also be easily removed.

Another feature of various embodiments of the invention provides an RFID tag that can be attached to objects of differing shapes. An additional feature of various embodiments of the invention provides an RFID tag that is operable to be affixed to various objects without adhesives.

To achieve the above-noted features, and in accordance with the purposes as embodied and broadly described herein, one exemplary embodiment provides a substantially cylindrically-shaped RFID tag. The substantially cylindrically-shaped RFID tag according to this embodiment comprises a substantially cylindrically-shaped structure, and an RFID transponder circuit secured to the substantially cylindrically-shaped structure.

In accordance with another exemplary embodiment, a reusable RFID tag is provided. The reusable RFID tag according to this embodiment comprises a substantially cylindrically-shaped structure, and an RFID circuit secured to the substantially cylindrically-shaped structure.

In accordance with a further exemplary embodiment, a method of manufacturing a reusable RFID identification tag is provided. The method according to this embodiment comprises encasing an RFID transponder circuit in a substantially cylindrically-shaped structure. An additional feature of an embodiment includes a method of re-using an RFID tag composing attaching a detachable RFID tag to a material. The material then encounters a radio frequency field and the RFID tag is activated. The method further includes removing the RFID tag from the material, processing the material, and then re-attaching the RFID tag to the material.

These and other embodiments and advantages of the present invention will become apparent from the following detailed description, taken in conjunction with the accompanying drawings, illustrating by way of example the principles of the invention.

BRIEF DESCRIPTION OF THE DRAWINGS

Purposes and advantages of the embodiments will be apparent to those of ordinary skill in the art from the following detailed description in conjunction with the appended drawings in which like reference characters are used to indicate like elements, and in which.

DETAILED DESCRIPTION

Figure 1:
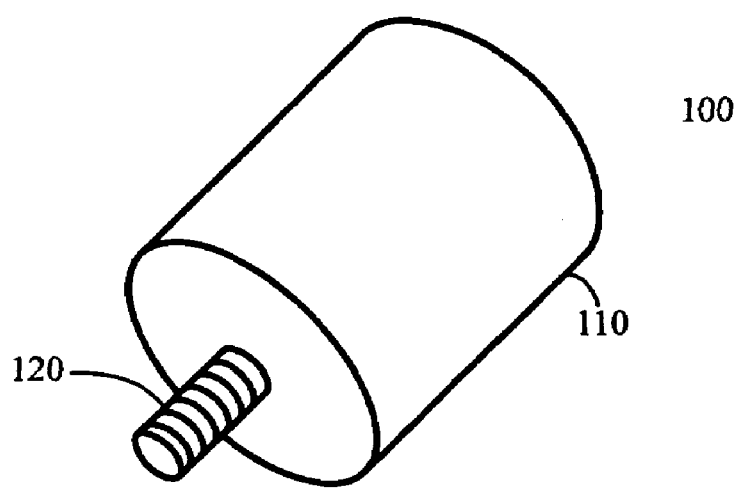
FIG. 1 is a perspective view of an exemplary button-type RFID tag according to various embodiments.

The following description is intended to convey a thorough understanding of the embodiments described by providing a number of specific embodiments and details involving a button-type RFID transponder tag and method of manufacturing a button-type RFID transponder tag. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design and other needs.

As used herein, the expressions "RFID tag" and "RFID transponder tag" will refer to any active or passive type of electronic data storage device, read-only or read and write, that is wirelessly activated in the presence of a radio frequency (RF) field, including any currently available inductively coupled RFID tags, capacitively coupled RFID tags and even future RF-type tags not yet available. This includes tags operating in the 125 kHz, 13.56 MHz, 868-927 MHz, 2.45 GHz and 5.8 GHz frequency bands as well as other suitable frequency bands. Also, the tag may be a silicon-type IC tag, a printed tag printed with a conductive ink-based printing process or a tag formed by other suitable means.

As used herein, the expressions and terms "surgical instrument," "medical instrument," "instrument," or "device" will refer to any type of surgical or medical instrument or portable equipment or device to which it may be desirable to attach an RFID tag. Though the specification is written in the context of medical and/or surgical instruments, it should be appreciated that the button-type RFID tag of the embodiments may be used with a variety of different items to be identified as shape and design constraints permit, including tools and equipment in other fields unrelated to the medical field. All of these uses are within the intended scope of the embodiments of the invention.

Throughout this description, the expression "button-type RFID tag" will be given broad meaning including, but not limited to, any type of RFID transponder tag that is encapsulated in a button-type module that includes an attachment portion for attaching the tag to items to be identified that have a reciprocal attachment portion. Preferably, the attachment is a threaded or a mating male/female attachment mechanism. In various other embodiments, the RFID transponder will be formed in an end portion of the tag, which will then be attached to a distal end of an instrument or device to be tagged, such as, for example, the handle of the instrument or device, during the later stages of the manufacturing process thereby eliminating the need to embed the tag in the device.

Described above are certain problems associated with the use of RFID tags on medical and/or surgical instruments. One proposed solution to the problem of RFID tags for surgical instruments and other surgical equipment has been to embed RFID transponder tags in a portion of the instrument at the time of manufacture. While ideal in theory, this solution may still suffer from some practical difficulties. First, this approach requires the tool or instrument to have been manufactured with the RFID tag inside. This is undesirable because it complicates the manufacturing process thereby increasing its expense, and it prohibits application of the technology to existing equipment through retrofitting. Second, the individual surgical instruments and equipment often have a high metal content. Because the tag is embedded in the metal, reading of the tag can be difficult due to losses in the metal of the electromagnetic signal. Finally, if the tag stops functioning, the entire instrument must be discarded, or else RF identification techniques can not be utilized with it. Thus, embedding still suffers from some significant technical obstacles.

Figure 2:
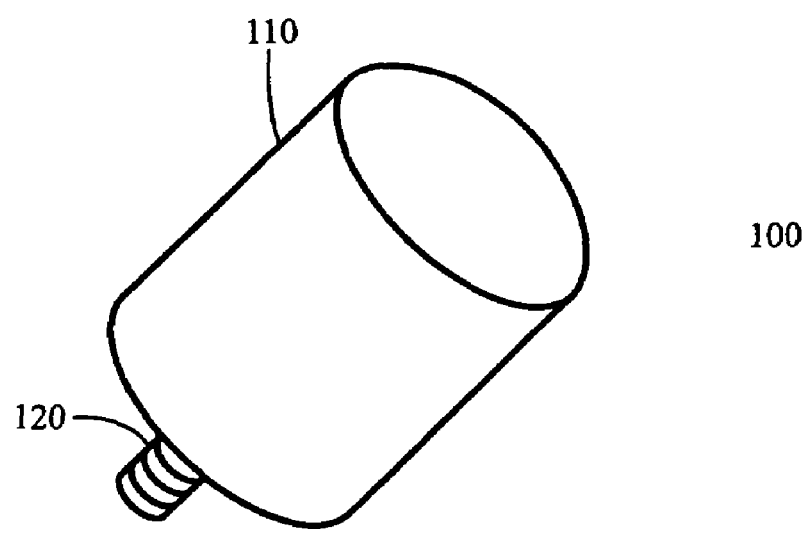
FIG. 2 is another perspective view of an exemplary button-type RFID tag according to various embodiments.

FIGS. 1 and 2 illustrate a button-type RFID transponder tag 100 in accordance with at least one exemplary embodiment of this invention. As shown in these FIGS., the button-type RFID transponder tag 100 comprises a button portion 110 and a threaded attachment portion 120. The tag 100 also comprises an RFID transponder circuit (not shown) that is formed inside the button portion 110. In various exemplary embodiments, the button portion 110 is cylindrically shaped and made of a substantially rigid material to protect the internal transponder circuit elements. However, in various other embodiments the button portion 110 may comprise a different shape, such as substantially square, rectangular, triangular or other geometric or non-geometric shape. In the view of FIG. 1, the RFID transponder circuit is invisibly contained in the button portion 110. However, in various exemplary embodiments, the RFID transponder circuit element may be externally visible as a bump, indentation or visible change of texture or composition of the button portion 110.

Though the tag's design will permit a single tag to be attached to devices of differing size, as long as the threaded attachment portion matches the dimensions of the reciprocal threaded attachment portion of the object, the tag may be manufactured with a threaded attachment portion formed in a plurality of different diameters and lengths to accommodate objects falling within various sizes and diameter ranges. The particular dimensions of the tag, including the ratio of the radius to the length, are not specific to the invention. In addition, the tag 100 shown in the Figures is a button-type tag having a circular cross-section, although any cross-section can be used in the embodiments. Other embodiments include tags whose cross-section varies throughout the length, as well as whose radius varies throughout the length. The expression "substantially cylindrically-shaped structure" includes cylindrically shaped structures having a circular cross-section, as well as other shell-type structures having non-circular cross-sections (e.g., oval, rectangular, square, triangular, octagonal, hexagonal, etc.). Those skilled in the art will be capable of designing a suitable tag for any given instrument, using the guidelines provided herein.

Also, though not shown in FIGS. 1 or 2, the outside surface of the button portion 110 of the tag 100 may have various visual indicia printed thereon including a numeric indicia, such as a part or item identification number, a textual indicia, such as a product name or product category name, or a brand indicia, such as a manufacturer name of the RFID tag or the item to which the tag is attached. In various exemplary embodiments, all three indicia are utilized. However, in various other embodiments, less than three indicia are utilized. In still further embodiments, more than three indicia are utilized or no indicia at all are utilized. In addition to these embodiments, other embodiments may utilize color coding, bar coding or other optically recognizable indicia. The embodiments are compatible with any of the aforementioned indicia schemes.

With continued reference to the button-type RFID tag 100 of FIG. 1, during practical application, an operator will screw the button-type tag 100 to a reciprocal threaded attachment portion associated with a portion of the object to be identified. In various embodiments, the object to be tagged will be preconfigured with a threaded attachment portion, such as, for example, a threaded recess. However, in various other embodiments, the button-type tag 100 will comprise a self-threading screw portion operable to puncture a surface of the object to be tagged when turned with sufficient axial pressure. Other attachment means include corresponding mating attachments, such as male/female snap-in type attachment mean, Velcro® or other hook and loop attachment means, or other mechanism capable of repeated attachment.

In various embodiments, the RFID transponder tag 100 is preprogrammed with identification information for the item that it will be attached to. Therefore, once tagged, the item may be wirelessly inventoried by activating the RFID transponder tag 100 using a suitable RF reader device. However, in various other embodiments, the tag will not be preprogrammed but rather is programmed after being attached to the object using an RFID writing or reading/writing device. Because RFID reader devices and reader/writer devices are well known in the art, a detailed discussion of such devices has been intentionally omitted. The button-type RFID transponder tag 100 according to a preferred embodiment is compatible with any suitable reader and/or reader/writer devices whether hand held, stationary, fixed or otherwise configured. Moreover, as will be discussed in greater detail herein, because the antenna portion of the tag preferably circumscribes the inside of the button portion 110, read failures due to improper orientation are greatly reduced and ideally eliminated.

Figure 3:
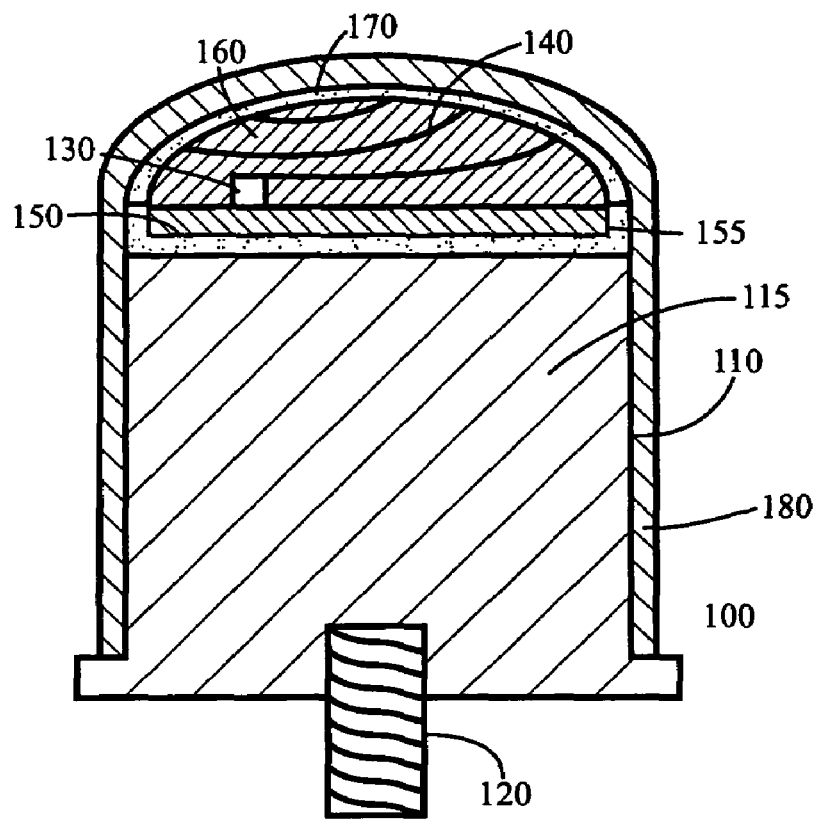
FIG. 3 is a cross-sectional diagram illustrating internal components of an exemplary button-type RFID tag according to various embodiments.

Referring now to FIG. 3, a cutaway side view of a button-type RFID transponder tag according to at least one embodiment of this invention is illustrated. As shown in FIG. 3, inside the button portion 110 is filler material 115, a recess 150 filled with an insulating material 170, a conductive base 155, an RFID processor 130, an antenna 140 and dielectric material 160, and a protective shroud 180. In various embodiments, the RFID processor 130 will be encased in a MSOP for integrated circuits package. Furthermore, as illustrated in the Figure, in various embodiments the antenna 140 will loop around the inner periphery of the button portion 110. Silicone or other insulating material 170 may be used to encapsulate the RFID circuit comprising the antenna 140, processor 130 and conductive base 155 within the tag and to prevent damage to these circuit components from heat, pressure, moisture, etc. As shown in FIG. 3, in various embodiments, a protective shroud 180 surrounds at least some of the button portion 110 to provide additional protection to the RFID circuit components. It should be noted that in a preferred embodiment the shroud 180 is not made of a metal material. Encasing the RFID tag in metal may reduce the ability to write to and read from the tag using an external device.

In various embodiments, the tag processor 130 contains read only memory. However, in various other embodiments, the tag processor 130 contains a read and write memory. In still further embodiments, the tag processor 130 contains a portion of memory that is permanent and a portion that may be written to.

Figure 4:
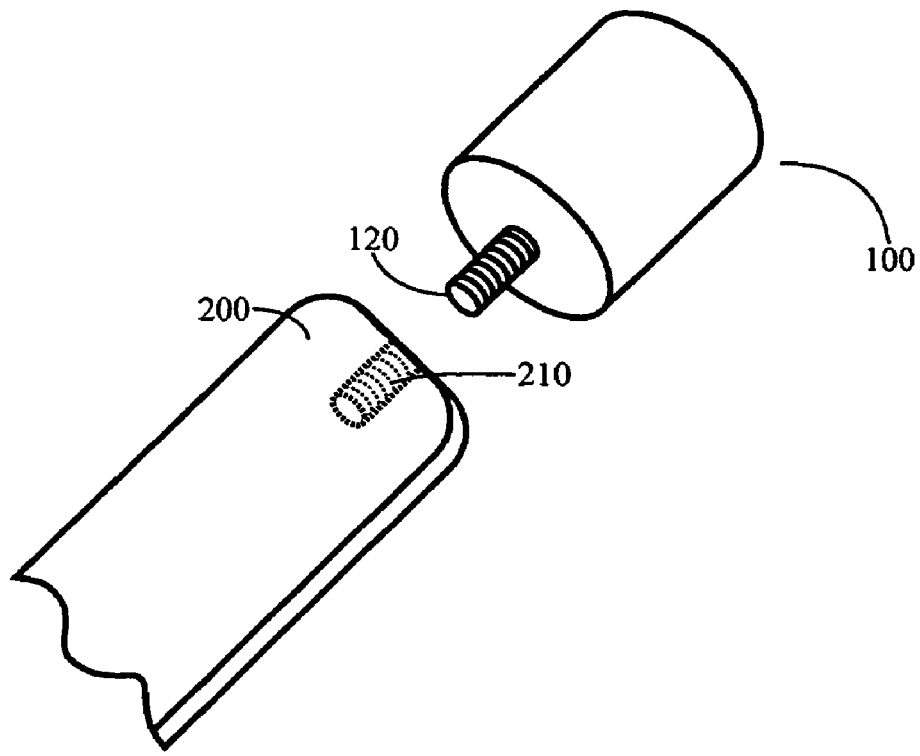
FIG. 4 is a perspective view of an exemplary button-type RFID tag illustrating a means in which the tag may be attached to an object to be identified according to various embodiments.

It should be appreciated that although the RFID circuit shown in FIG. 3 is located at the top of the button portion 110, this location is for purposes of example only. In various embodiments the RFID circuit may be located elsewhere on or within the button portion 110. Such modifications are within the scope of this invention;

FIG. 4 illustrates a perspective view of a button-type RFID tag and an instrument. The threaded attachment portion 120 of the button-type tag 100 is screwed into the threading receiving portion 210 of the instrument. In various embodiments the instrument 200 can be a surgical instrument such as, for example, a scalpel, forceps, retractor, etc. However, in various other embodiments, the instrument 200 will be a different instrument, device, equipment or other item to be identified. Once attached to the instrument 200, the button-type tag 100, if not already programmed, may be programmed to contain identification information for that instrument. Subsequent to this, the instrument may be identified and/or other information such as date of first use, date of sterilization, date of manufacture, part number, manufacturer name and/or id, etc., may be read from the tag 100 using any suitable RFID reading device. Though the tag 100 may be simply removed by unscrewing it from the instrument 200, it is preferred in an embodiment that the tag 100 remain attached to the instrument for the useful life of the instrument and/or tag, at all times, including during sterilization, normal use, storage, etc. By encasing the RFID circuit within the protective button housing 110, the circuitry will be able to withstand the rigors of harsh sterilization environments without damage. However, a feature of the invention is that because the button-type tag 100 is attached to the instrument 200 using a detachable attachment mechanism, should the tag 100 become non-functional, it may simply be removed from the instrument 200, discarded, and replaced with a new tag, in contrast to RFID tags that are embedded in a handle or other portion of the instrument. Alternatively, the tag 100 may be detached and re-attached to the same or different objects, for example, during sterilization or other procedures.

Figure 5:
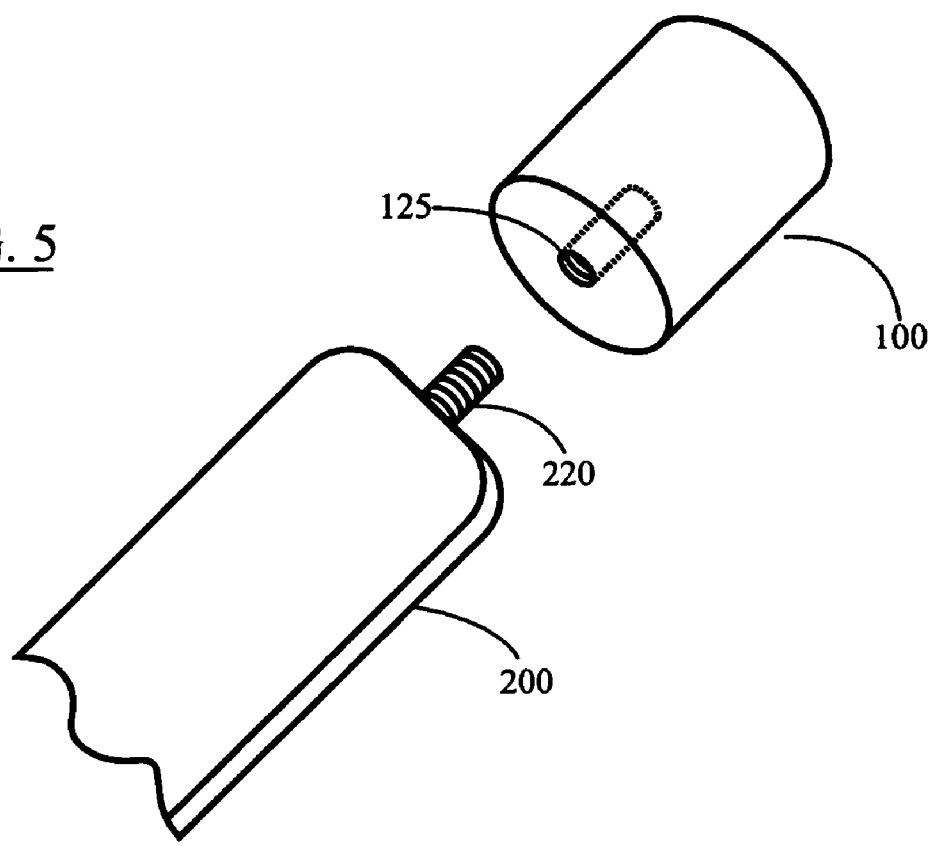
FIG. 5 is a perspective view of another exemplary button-type RFID tag illustrating different means for attaching the tag to an object to be identified according to various embodiments.

Referring now to FIG. 5, a perspective view of another button-type RFID tag and an instrument according to at least one embodiment is illustrated. Unlike the embodiment illustrated in FIG. 4, in the embodiment of FIG. 5, the button-type RFID tag 100 is configured with a threaded receiving portion 125 adapted to mate with a threaded member 220 of an instrument 200 or other equipment. Having the threaded member on the instrument rather than the tag may reduce the manufacturing costs of the tag increasing resistance to adoption of the button-type RFID tag.

Figure 6:
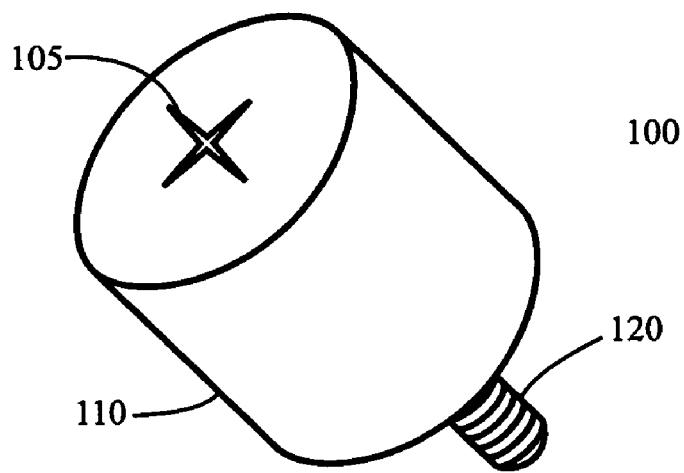
FIG. 6 is a perspective view of another exemplary button-type RFID tag illustrating an integrated mechanical attachment means.

Referring now to FIG. 6, a perspective view of a button-type RFID tag according to at least one embodiment is illustrated. In the embodiment of FIG. 6, the tag 100 is illustrated having a cross-shaped recess 105 in a top surface of the button portion 110. The purpose of the cross-shaped recess 105 is to allow for machine attaching of the tag 100 to an instrument or other item to be tagged. The cross-shaped recess 105 is adapted to receive a Phillips head screwdriver or Phillips-tipped bit. However, it should be appreciated that other shapes maybe used without departing from the spirit or scope of the invention, such as, for example, a slotted-screw slot, a hexagonal opening, a star-shaped opening, or other suitable shaped opening. Alternatively, the button portion 110 itself may be shaped in a hexagonal or square shaped such that it can be attached using a torque wrench.

It should be noted that in the embodiments discussed thus far, the tag is contemplated as a separately manufactured stand-alone tag that is manually, or mechanically attached to instruments or other objects to be identified. However, it will be appreciated that alternatively, the tag may be attached to the instrument during the instrument's manufacturing process in a permanent or semi-permanent manner. After attachment to the instrument both the tag and instrument could be encapsulated in a suitable encapsulating material to prevent the tag and instrument from becoming unintentionally detached.

Figure 7:
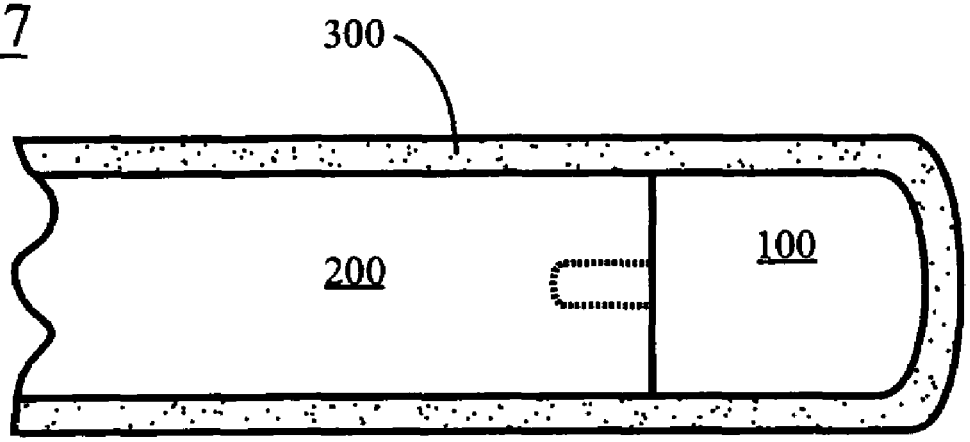
FIG. 7 is a cross sectional view of another exemplary button-type RFID illustrating an attachment means in which the button-type tag is physically attached using a threaded member and then encapsulated with an encapsulating substance to create a unified structure according to various embodiments.

Referring now to FIG. 7, a cut away view of a button-type RFID tag and instrument formed as a unitary structure according to at least one embodiment of this invention is illustrated. In the embodiment shown in FIG. 7, a button-type RFID tag 100 is mated with an instrument 200 using a threaded attachment member. Though in the embodiment of FIG. 7, the tag 100 is shown as having the threaded attachment member, it should be appreciated that as discussed herein, the tag may merely have a threaded recess, while the threaded member is located on the instrument. The tag 100 and instrument 200 structure are encased in an encapsulating material 300.

In various embodiments, the tag 100 and instrument 200 are joined during manufacture of the instrument through an automated process and then encased using an encapsulating material 300 such as, for example, silicone, rubber, resin, or other suitable material. This method of attachment has several advantages. Firstly, the tag 100 and instrument may be attached using automated manufacturing processes. Secondly, by encasing both items the chances of them becoming unintentionally detached is significantly decreased. Thirdly, by encasing them in a encasing material 300, the tag 100 and instrument 200 become a unitary structure that may enhance the ability to manipulate the instrument manually and also improve the aesthetics by concealing the tag 100—instrument 200 seam. In a preferred embodiment, the encasing material will have an increased coefficient of friction and/or texture so as to make the combined structure easer to grip and manipulate with the hands.

It should be appreciated that while various embodiments of the invention describe a button-type RFID transponder tag having a threaded portion in either the form of a threaded member or a threaded socket, that an unthreaded member or socket may also be utilized with various embodiments of the invention in which a compression-type fitting is provided between the tag and the item to be identified. For example, either the tag or item to be identified may be configured with a spherically-shaped ball attached to a post which is inserted to a rounded socket to provide a friction-based connection.

Moreover, though not illustrated in the Figures, in various embodiments, the button-type RFID transponder tag will comprise both a threaded member and a threaded socket, allowing the tag to serve as a pass through device. For example, certain medical equipment, such as, medical scalpels and other knives, comprise a blade portion and a handle connected to one another by a threaded connection. Thus, by having both male and female threaded members integrated into the button-type tag housing, the tag may resided between instrument components utilizing a connection interface already existing between these items. Such embodiments may have particular utility for retrofitting the button-type RFID tag according to various embodiments of the invention to existing equipment.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. A button-type RFID tag comprising:
 a substantially cylindrically-shaped structure; and
 an RFID transponder circuit secured to the structure, wherein the substantially cylindrically-shaped structure comprises a threaded attachment portion that mates with a complimentary threaded attachment portion at a distal end of a surgical instrument handle, thereby allowing the tag to be detachably affixed to the surgical instrument.

2. The tag according to claim 1, wherein a memory structure in the RFID transponder circuit the tag stores identification information as well as processing history information for the instrument to which the tag is attached though the life cycle of the instrument.

3. The tag according to claim 1, wherein the threaded attachment portion comprises a threaded screw member.

4. The tag according to claim 1, wherein the threaded attachment portion comprises a threaded recess.

5. The tag according to claim 1, wherein the transponder circuit is formed on a portion of the structure.

6. The tag according to claim 1, wherein the transponder circuit comprises an antenna, a microprocessor and a digital memory.

7. The tag according to claim 6, wherein the memory is operable to store identification information for at least one item that the tag is associated with.

8. The tag according to claim 6, wherein the memory comprises a read only portion and a writable portion.

9. The tag according to claim 6, wherein the antenna is a wire antenna that circumscribes a portion of the substantially cylindrically-shaped structure.

10. The tag according to claim 1, wherein at least a portion of the RFID transponder circuit is encapsulated in a protective material.

11. The tag according to claim 10, wherein the protective housing comprises a material selected from the group consisting of plastic, metal, metal alloy and other pressure resistant material.

12. The tag according to claim 1, further comprising an outermost shroud portion.

13. The tag according to claim 12, wherein the outermost shroud portion comprises a recess adapted to receive a turning tool.

14. The tag according to claim 1, further comprising one or more visual indicia on an outward facing surface of the substantially cylindrically-shaped structure.

15. The tag according to claim 14, wherein the one or more indicia is selected from the group consisting of a brand owner name, a product name, a category name, a color code, a graphic image, a product identification number, a bar code and combinations thereof.

16. A removable RFID tag comprising:
a substantially cylindrically-shaped structure; and
an RFID circuit secured to the structure, wherein the substantially cylindrically-shaped structure comprises a threaded attachment portion that mates with a complimentary threaded attachment portion at a distal end of a surgical instrument handle, thereby allowing the tag to be removably affixed to the surgical instrument.

17. The tag according to claim 16, wherein a memory structure in the RFID circuit stores identification information as well as processing history information for the instrument to which the tag is attached though the life cycle of the instrument.

18. The tag according to claim 16, wherein the threaded attachment portion comprises a threaded screw member.

19. The tag according to claim 16, wherein the threaded attachment portion comprises a threaded recess.

20. The tag according to claim 16, wherein the transponder circuit is formed on a portion of the structure.

21. The tag according to claim 16, wherein the transponder circuit comprises an antenna, a microprocessor and a digital memory.

22. The tag according to claim 21, wherein the memory is operable to store identification information for at least one item that the tag is associated with.

23. The tag according to claim 21, wherein the memory comprises a read only portion and a writable portion.

24. The tag according to claim 21, wherein the antenna is a wire antenna that circumscribes a portion of the substantially cylindrically-shaped structure.

25. The tag according to claim 16, wherein at least a portion of the RFID transponder circuit is encapsulated in a protective material.

26. The tag according to claim 25, wherein the protective housing comprises a material selected from the group consisting of plastic, metal, metal alloy and other pressure resistant material.

27. The tag according to claim 16, further comprising an outermost shroud portion.

28. The tag according to claim 27, wherein the outermost shroud portion comprises a recess adapted to receive a turning tool.

29. The tag according to claim 16, further comprising one or more visual indicia on an outward facing surface of the substantially cylindrically-shaped structure.

30. The tag according to claim 29, wherein the one or more indicia is selected from the group consisting of a brand owner name, a product name, a category name, a color code, a graphic image, a product identification number, a bar code and combinations thereof.

31. A method of rendering a surgical instrument identifiable with an RFID reader comprising:
attaching substantially cylindrically-shaped housing containing an RFID tag circuit to a distal end of a surgical instrument handle using a threaded attachment mechanism aligned along a long axis of the handle;
programming identification information corresponding to the surgical instrument in a memory structure in the RFID tag; and
programming additional processing information in the memory structure when the instrument is processed in or out of an instrument processing facility over the life cycle of the instrument.

* * * * *